United States Patent [19]

Koike et al.

[11] 4,267,317
[45] May 12, 1981

[54] PROCESS FOR PRODUCING PHENOXYALKENE DERIVATIVE

[75] Inventors: Wataro Koike; Tadashi Sasuga, both of Shizuoka; Chihiro Yazawa, Yokohama, all of Japan

[73] Assignee: Ihara Chemical Industry Co., Ltd., Tokyo, Japan

[21] Appl. No.: 84,161

[22] Filed: Oct. 12, 1979

[30] Foreign Application Priority Data

Nov. 14, 1978 [JP] Japan ............................... 53-140284
Feb. 22, 1979 [JP] Japan ............................... 54-19099

[51] Int. Cl.³ .................... C07C 69/76; C07C 69/767; C07C 59/48
[52] U.S. Cl. ................................... 542/416; 546/286; 546/287; 546/288; 546/297; 546/301; 546/302; 560/61; 562/471; 260/465 D; 260/465 F; 260/455 R
[58] Field of Search .................... 560/61; 562/471; 546/286, 287, 297, 288, 301, 302; 542/416; 260/465 D, 465 F, 455 R

[56] References Cited

U.S. PATENT DOCUMENTS 3,972,887  8/1976  Freedman ............................... 546/25

OTHER PUBLICATIONS

McKillop et al., Chemical Abstracts, vol. 81, No. 23, 151,696e, Dec. 9, 1974.
Buehler et al., Survey of Organic Synthesis, Wiley-Interscience Pub., pp. 75-77, (1970).

*Primary Examiner*—Alan L. Rotman
*Attorney, Agent, or Firm*—Oblon, Fisher, Spivak, McClelland & Maier

[57] ABSTRACT

A phenoxyalkene derivative having the formula

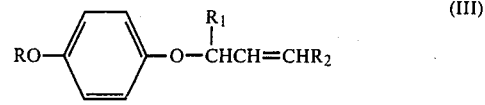

wherein R represents a hydrogen atom,

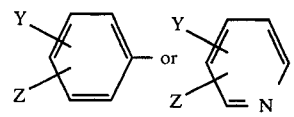

and Y and Z are the same or different and respectively represent a hydrogen atom, trifluoromethyl group, a halogen atom, a lower alkyl group, nitro group or cyano group; $R_1$ represents a hydrogen atom or a lower alkyl group and $R_2$ represents carboxyl, hydroxymethyl, allyloxycarbonyl, a lower alkoxycarbonyl, a lower haloalkoxycarbonyl, a S-lower alkylthiocarbonyl, carbamoyl, a N-lower alkylcarbamoyl or a N-phenylcarbamoyl group is produced by reacting a phenol compound having the formula

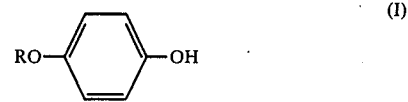

with a dihalogen compound having the formula

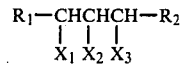

wherein R, $R_1$ and $R_2$ are defined above and $X_1$ represents a halogen atom and $X_2$ and $X_3$ are different and respectively represent a hydrogen atom or a halogen atom, by a simultaneous reaction of an etherification and an unsaturated double bond formation, in the presence of a dehydrogenhalide agent and a polar solvent or a combination of a nonpolar solvent and a quaternary ammonium salt or a quaternary phosphonium salt.

4 Claims, No Drawings

PROCESS FOR PRODUCING PHENOXYALKENE DERIVATIVE

BACKGROUND OF THE INVENTION

1. Field of the Invention

The present invention relates to a process for producing phenoxyalkene derivatives useful as agricultural chemicals.

2. Description of the Prior Art

It has been known that phenoxyalkene derivatives can be produced by reacting a phenol having the formula

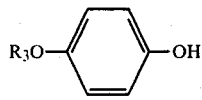

wherein $R_3$ represents hydrogen atom or

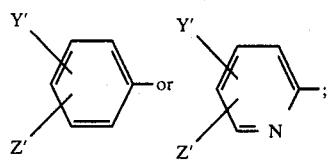

$Y'$ and $Z'$ are the same or different and respectively represent hydrogen atom, trifluoromethyl group, a halogen atom, or lower alkyl group, nitro group or cyano group, with a monohalogen compound having the formula

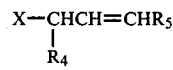

wherein $R_4$ represents a lower alkyl group; $R_5$ represents carboxyl, hydroxymethyl, allyloxycarbonyl, a lower alkoxycarbonyl, a lower haloalkoxycarbonyl, a S-lower alkylthiocarboxyl, carbamoyl, a N-lower alkylcarbamoyl or a N-phenylcarbamoyl group in a solvent such as ketones e.g. acetone, and methylethyl ketone, ethers such as tetrahydrofuran, diethyl ether, methyl butyl ether, ethyleneglycol dimethyl ether; dimethylformamide, dimethylacetamide, dimethylsulfoxide, benzene, toluene and hexane, etc. in the presence of a dehydrogenhalide agent such as an alkali metal compound e.g. sodium or potassium compound or an alkaline earth metal compound e.g. calcium or magnesium compound.

However, a dehydrogenhalidation of the monohalogen compound is caused by this process. Thus, a large amount of the monohalogen compound should be used and a large amount of the by-products is produced to cause low yield of the object compound.

The inventors have studied to obtain a phenoxyalkene derivative having high purity in high yield. Thus, the special reaction mechanism of combination of an etherification and an unsaturated double bond formation in one step has been found.

SUMMARY OF THE INVENTION

It is an object of the present invention to produce a phenoxyalkene derivative having high purity in high yield by a special reaction mechanism.

The foregoing and other objects of the present invention have been attained by reacting a phenol compound having the formula

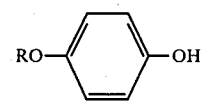

wherein R represents a hydrogen atom,

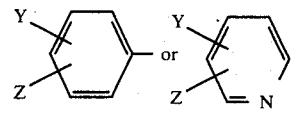

and Y and Z are the same or different and respectively represent a hydrogen atom, trifluoromethyl group, a halogen atom, a lower alkyl group, nitro group or cyano group; with a dihalogen compound having the formula

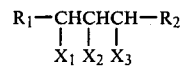

wherein $R_1$ represents a hydrogen atom or a lower alkyl group; $R_2$ represents carboxyl, hydroxymethyl, allyloxycarbonyl, a lower alkoxycarbonyl, a lower haloalkoxycarbonyl, a S-lower alkylthiocarboxyl, carbamoyl, a N-lower alkylcarbamoyl or a N-phenylcarbamoyl group; $X_1$ represents a halogen atom, $X_2$ and $X_3$ are different and respectively represent a hydrogen atom or a halogen atom in a solvent in the presence of a dehydrogenhalide agent of an alkali metal compound or an alkaline earth metal compound to obtain a phenoxyalkene derivative having the formula

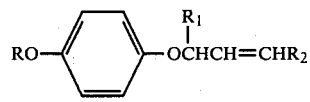

wherein R, $R_1$ and $R_2$ are defined above.

It is preferable to add a quarternary ammonium salt such as benzyltrialkyl ammonium salt and tetraalkyl ammonium salt or a quaternary phosphonium salt such as benzyltrialkyl phosphonium salt and tetraalkyl phosphonium salt in a nonpolar solvent.

It is also preferable to carry out the reaction in a polar solvent without a quaternary salt.

DETAILED DESCRIPTION OF THE PREFERRED EMBODIMENTS

The reaction mechanism of the present invention is a novel mechanism of a combination of an etherification and an unsaturated double bond formation.

The phenols having the formula (I) are the compounds having the formula

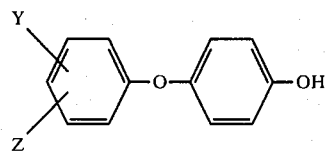

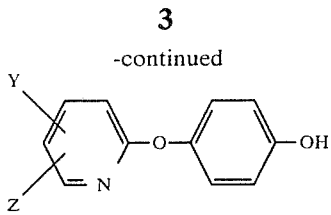

wherein Y and Z are the same or different and respectively represent a hydrogen atom, trifluoromethyl group, a halogen atom such as chlorine, bromine, fluorine or iodine atom; a lower alkyl group e.g. methyl, ethyl, propyl, isopropyl, butyl and isobutyl group; nitro group and cyano group.

The dihalogen compounds used in the present invention include the compounds having the formula (II) wherein $R_1$ represents a hydrogen atom; a lower alkyl group such as methyl, ethyl, propyl, isopropyl, butyl and isobutyl group; $R_2$ represents carboxyl, hydroxymethyl, allyloxycarbonyl; a lower alkoxycarbonyl such as methoxycarbonyl, ethoxycarbonyl, isopropoxycarbonyl and sec.-butoxycarbonyl group; a lower haloalkoxycarbonyl group such as $\beta$-chloroethoxycarbonyl, $\beta$-bromoethoxycarbonyl, $\alpha,\beta$-dibromopropyloxycarbonyl, and $\beta$, $\beta'$-dibromoisopropyloxycarbonyl group; a S-lower alkylthiocarboxyl group such as S-methylthiocarboxyl, S-ethylthiocarboxyl and S-butylthiocarboxyl group; carbamoyl group; a N-lower alkylcarbamoyl group such as N-methylcarbamoyl, N-ethylcarbamoyl, N-isopropylcarbamoyl and N-isobutylcarbamoyl group; N-phenylcarbamoyl group; $X_1$ represents a halogen atom and $X_2$ and $X_3$ are different and respectively represent a hydrogen atom or a halogen atom.

When the reaction of the present invention is carried out in a polar solvent, the polar solvent can be a lower alcohol such as methanol and ethanol; ketones such as acetone, methylethyl ketone; ethers such as tetrahydrofuran, diethyl ether, methyl butyl ether, ethyleneglycol dimethylether, dimethylformamide, dimethylacetamide, and dimethylsulfoxide.

Sometimes, it is preferable to add a quaternary ammonium salt or a quaternary phosphonium salt such as benzyltrialkylammonium salts, benzyltrialkylphosphonium salts, tetraalkylammonium salts and tetraalkylphosphonium salts, for example, benzyltriethylammonium bromide, benzyltributylammonium chloride, benzyltriamylammonium chloride, benzyltrioctylammonium chloride, trioctylmethylammonium chloride, isobutyltributylammonium bromide, hexadecyltributylphosphonium bromide, tetrapropylammonium bromide, tetrabutylammonium bromide, tetrabutylammonium chloride, tetraamylammonium bromide, tetraamylammonium chloride, tetrahexylammonium bromide, tetrabutylphosphonium chloride, benzyltributylphosphonium chloride, benzyltriphenylphosphonium chloride, methyltriphenylphosphonium bromide and tetraphenylphosphonium chloride. It is preferable to select the quaternary ammonium salt or the quaternary phosphonium salt from benzyl tri-$C_1$-$C_{16}$ alkylammonium salts, tetra-$C_1$-$C_{16}$ alkylammonium salts, triphenyl $C_1$-$C_{16}$ alkylammonium salts, benzyl tri-$C_1$-$C_{16}$ alkylphosphonium salts, tetra-$C_1$-$C_{16}$ alkylphosphonium salts, and triphenyl $C_1$-$C_{16}$ alkylphosphonium salts.

The alkali metal compounds or alkaline earth metal compounds used in the reaction can be potassium hydroxide, sodium hydroxide, potassium carbonate, sodium carbonate and sodium bicarbonate.

It is preferable to use a solvent so as to smoothly perform the reaction, especially to use a solvent being stable in the reagents including the alkali metal compound and the alkaline earth metal compound.

In the reaction of the present invention, the dihalogen compound (II) is used at a molar ratio of 1.0 to 1.5 preferably 1.05 to 1.1 based on the phenol compound (I).

The alkali metal compound or the alkaline earth metal compound as a base is used at a molar ratio of 1 to 3 based on the phenol compound (I). The alkali metal compound or the alkaline earth metal compound can be used as an aqueous solution.

The quaternary ammonium salt or the quaternary phosphonium salt is used as a molar ratio of 0.005 to 0.05 preferably 0.008 to 0.015 based on the phenol compound (I).

In the reaction of the phenol compound (I) with the dihalogen compound (II), the reaction temperature can be 30° to 150° C. preferably 60° to 120° C. in a polar solvent and 50° to 90° C. preferably 60° to 80° C. in a nonpolar solvent presence of a quaternary salt.

The reaction time can be in a range of 4 to 8 hours. When the quaternary salt is used, after the reaction, the water phase is separated and the organic phase is washed with an acid and then with water and then, the solvents are removed by a distillation under a reduced pressure to obtain the object compound of the phenoxyalkene derivative (III).

When the quaternary salt is not used, a polar solvent is used, after the reaction, the solvent is distilled off and the resulting product was dissolved in a nonpolar solvent such as benzene, toluene, chlorobenzene and the solution is washed with water. The water phase is separated and the resulting organic phase is washed with an acid and then with water and then, the solvents are removed by a distillation under a reduced pressure to obtain the object compound of the phenoxyalkene derivative (III).

When the dihalogen compound (II) is not an ester, after the reaction, a conc. hydrochloric acid is added with stirring to be acidic and the water phase is separated and then, the solvent is distilled off to obtain the phenoxyalkene derivative (III).

In accordance with the process of the present invention, the phenol compound (I) and the dihalogen compound having saturated hydrocarbon chain (II) is used to react them in a novel reaction mechanism for preventing a side reaction and performing the etherification and the unsaturated double bond formation, whereby the object compound of the phenoxyalkene derivative having high purity can be obtained in high yield.

The present invention will be further illustrated by certain examples and references which are provided for purposes of illustration only and are not intended to be limiting the present invention.

EXAMPLE 1

In a reactor, 15 g of chlorobenzene and 15 g of water were charged, and 12.7 g (0.05 mole) of 4-(4-trifluoromethylphenoxy)phenol, 15.8 g (0.055 mole) of ethyl 3,4-dibromopentanoate and 8.7 g (0.063 mole) of potassium carbonate and 0.3 g (0.001 mole) of tributylethylammonium bromide were added. They were refluxed for 6 hours to react them. The water phase was separated and the organic phase was washed with 5% hydrochloric acid and with water and then, chlorobenzene, ethyl 3,4-dibromopentanoate and low boiling by-products were distilled off at 100° C. under a reduced pressure (0.02–0.05 mmHg) to obtain 18.1 g of ethyl 4-[4-(4-trifluoromethylphenoxy)phenoxy]-2-pentenoate ($n_D^{20}$ 1.5175). The yield was 95.1%.

The same process was repeated to obtain the same compound except using ethyl 3,4-dichloropentanoate 10.9 g (0.055 mole) instead of ethyl 3,4-dibromo-pentanoate 15.8 g (0.055 mole). The yield was 83.1%.

EXAMPLE 2

In a reactor, 15 g of toluene and 15 g of water was charged in a reactor and then, 12.7 g (0.05 mole) of 4-(4-trifluoromethylphenoxy)phenol, 14.3 g (0.055 mole) of 3,4-dibromopentanoic acid, 16.6 g (0.12 mole) of potassium carbonate and 0.23 g (0.001 mole) of triethylbenzylammonium chloride were added. They were refluxed for 6 hours to react them and then, conc. hydrochloric acid was added to the reaction mixture with stirring to be acidic and then, the water phase was separated and the organic phase was washed with water and then, toluene and low boiling by-products were distilled off at 100° C. under a reduced pressure (0.02–0.05 mmHg) to obtain 14.8 g of 4-[4-(4-trifluoromethylphenoxy)phenoxy]-2-pentenoic acid ($n_D^{20}$ 1.5284). The yield was 84.2%.

REFERENCE 1

In accordance with the process of Example 1 except using tributylethylammonium bromide, the reagents were refluxed for 6 hours to react them and the reaction mixture was cooled to the room temperature and 2 g (0.05 mole) of sodium hydroxide was added and then, the mixture was further stirred for 30 minutes. The mixture was treated as the process of Example 1 to obtain 6.0 g of ethyl 4-[4-(trifluoromethylphenoxy)phenoxy]-2-pentenoate. The yield was 31.5%.

REFERENCE 2

In accordance with the process of Example 1 except that tributylethylammonium bromide was not used and ethyl 3,4-dibromo-pentanoate is replaced to 11.4 g (0.055 mole) of ethyl 4-bromo-2-pentenoate, the reagents were refluxed for 6 hours to react them, and the reaction mixture was cooled to the room temperature and 2 g (0.05 mole) of sodium hydroxide was added and then, the mixture was further stirred for 30 minutes. The mixture was treated as the process of Example 1 to obtain 5.9 g of ethyl 4-[4-(4-trifluoromethylphenoxy)phenoxy]-2-pentenoate. The yield was 31.0%.

EXAMPLE 3

In a reactor, 30 g of ethanol was charged and 12.7 g (0.05 mole) of 4-(4-trifluoromethylphenoxy)phenol, 15.8 g (0.055 mole) of ethyl 3,4-dibromopentanoate, 8.7 g (0.063 mole) of potassium carbonate were charged. They were refluxed for 6 hours to react them. After the reaction, ethanol was distilled off from the reaction mixture and then 50 ml of toluene was added to the resulting mixture, and resulting solution was washed with water and then, the organic phase was washed with 5% hydrochloric acid and with water and then ethyl 3,4-dibromopentanoate and a lower boiling by-products were distilled off at 100° C. under a reduced pressure of 0.02–0.05 mmHg to obtain 15.6 g of ethyl 4-[4-(4-trifluoromethylphenoxy)phenoxy]-2-pentenoate ($n_D^{20}$ 1.5175). The yield was 82.0%. The same process was repeated to obtain same compound except using ethyl 3,4-dichloropentanoate 10.9 g (0.055 mole) instead of ethyl 3,4-dibromopentanoate 15.8 g (0.055 mole). The yield was 73.6%.

REFERENCE 3

In accordance with the process of Example 3 except using 30 g of chlorobenzene instead of 30 g of ethanol, the reagents were refluxed for 6 hours to react them and the mixture was cooled to the room temperature and 2 g (0.05 mole) of sodium hydroxide was added and then, the mixture was further stirred for 30 minutes. The mixture was treated as the process of Example 1 to obtain 6.0 g of ethyl 4-[4-(4-trifluoromethylphenoxy)phenoxy]-2-pentenoate. The yield was 31.5%.

EXAMPLE 4

In a reactor, 30 g of tetrahydrofuran was charged and 12.7 g (0.05 mole) of 4-(4-trifluoromethylphenoxy)phenol, 14.3 g (0.055 mole) of 3,4-dibromopentanoic acid and 16.6 g of potassium carbonate were charged. They were refluxed for 6 hours to react them. After the reaction, tetrahydrofurane was distilled off from the reaction mixture and then 50 ml of chlorobenzene was added to the resulting mixture and then conc. hydrochloric acid was added to the resulting mixture with stirring to be acidic and then, the water phase was separated and the organic phase washed with water and then, chlorobenzene and low boiling by-products were distilled off at 100° C. under a reduced pressure (0.02–0.05 mmHg) to obtain 13.2 g of 4-[4-(4-trifluoromethylphenoxy)phenoxy]-2-pentenoic acid. ($n_D^{20}$ 1.5284). The yield was 75%.

EXAMPLES 5 to 78

In accordance with the process of Example 1 or 3 except varying the kinds of the phenol compound and the dihalogen compounds, the corresponding derivatives were produced. The results are shown in Table 1 wherein the corresponding process to Example 1 using tributylethylammonium bromide is referred to as Reaction 1 and the corresponding process to Example 3 using a polar solvent of ethanol is referred to as Reaction 2.

TABLE 1

| Example | | Starting materials | | | | Yield (%) | |
| Reaction 1 | Reaction 2 | Phenol compound | Dihalogen compound | Product Phenoxyalkene derivative | Physical property | Reaction 1 | Reaction 2 |
| --- | --- | --- | --- | --- | --- | --- | --- |
| 5 | 42 | 4-(4-chlorophenoxy)phenol | n-butyl 2,4-dibromopentanoate | n-butyl 4-[4-(4-chlorophenoxy)phenoxy]-2-pentenoate | $n_D^{20}$ 1.5547 | 95.2 | 84.5 |
| 6 | 43 | 4-(2,4-dichlorophenoxy)phenol | 3,4-dibromopentanoic acid | 4-[4-(2,4-dichlorophenoxy)phenoxy]-2-pentenoic acid | m.p. 79–81° C. | 86.6 | 78.0 |
| 7 | 44 | 4-(4-bromo-2-chlorophenoxy)phenol | i-propyl 3,4-dibromopentanoate | i-propyl 4-[4-(4-bromo-2-chlorophenoxy)phenoxy]- | $n_D^{20}$ 1.5710 | 96.0 | 83.0 |

TABLE 1-continued

Starting materials

| Example Reaction 1 | Example Reaction 2 | Phenol compound | Dihalogen compound | Product Phenoxyalkene derivative | Physical property | Yield (%) Reaction 1 | Yield (%) Reaction 2 |
|---|---|---|---|---|---|---|---|
| 8 | 45 | 4-(3,5-dichloropyridyl-2-oxy)phenol | ethyl 3,4-dibromopentanoate | ethyl 4-[4-(3,5-dichloropyridyl-2-oxy)phenoxy]-2-pentenoate | $n_D^{20}$ 1.5697 | 95.5 | 86.0 |
| 9 | 46 | 4-(2-trifluoromethylphenoxy)phenol | ethyl 3,4-dibromohexanoate | ethyl 4-[4-(2-trifluoromethylphenoxy)phenoxy]-2-hexenoate | $n_D^{20}$ 1.5031 | 94.4 | 81.6 |
| 10 | 47 | 4-(4-trifluoromethylphenoxy)phenol | allyl 2,4-dichloropentanoate | allyl 4-[4-(trifluoromethylphenoxy)phenoxy]-2-pentenoate | $n_D^{20}$ 1.5218 | 79.0 | 70.0 |
| 11 | 48 | 4-(4-trifluoromethylphenoxy)phenol | n-butyl 3,4-dichloropentanoate | n-butyl 4-[4-(4-trifluoromethylphenoxy)phenoxy]-2-pentenoate | $n_D^{20}$ 1.5137 | 82.1 | 72.5 |
| 12 | 49 | 4-(4-trifluoromethylphenoxy)phenol | ethyl 3,4-dibromopentanethioate | ethyl 4-[4-(4-trifluoromethylphenoxy)phenoxy]-2-pentenethioate | $n_D^{20}$ 1.5365 | 93.3 | 83.1 |
| 13 | 50 | 4-(4-trifluoromethylphenoxy)phenol | 3,4-dibromopentanoic amide | 4-[4-(4-trifluoromethylphenoxy)phenoxy]-2-pentenoic amide | m.p. 140–142° C. | 81.6 | 71.0 |
| 14 | 51 | 4-(4-trifluoromethylphenoxy)phenol | n-octyl 3,4-dibromopentanoate | n-octyl 4-[4-(4-trifluoromethylphenoxy)phenoxy]-2-pentenoate | $n_D^{20}$ 1.5045 | 91.1 | 80.8 |
| 15 | 52 | 4-(4-trifluoromethylphenoxy)phenol | sec.-butyl 2,4-dichloropentanoate | sec.-butyl 4-[4-(4-trifluoromethylphenoxy)phenoxy]-2-pentenoate | $n_D^{20}$ 1.5112 | 80.8 | 74.0 |
| 16 | 53 | 4-(4-iodophenoxy)phenol | ethyl 4-bromo-3-chloropentanoate | ethyl 4-[4-(4-iodophenoxy)phenoxy]-2-pentenoate | $n_D^{20}$ 1.5877 | 95.3 | 86.3 |
| 17 | 54 | 4-(4-bromophenoxy)phenol | ethyl 3,4-dibromopentanoate | ethyl 4-[4-(4-bromophenoxy)phenoxy]-2-pentenoate | $n_D^{20}$ 1.5708 | 95.5 | 84.5 |
| 18 | 55 | 4-(4-trifluoromethylphenoxy)phenol | n-butyl 3,4-dibromopentanethioate | n-butyl 4-[4-(4-trifluoromethylphenoxy)phenoxy]-2-pentenethioate | $n_D^{20}$ 1.5156 | 91.6 | 85.8 |
| 19 | 56 | 4-(2-bromophenoxy)phenol | 3,4-diiodopentanoic N-isopropylamide | 4-[4-(2-bromophenoxy)phenoxy]-2-pentenoic N-isopropylamide | m.p. 127–128° C. | 80.3 | 74.3 |
| 20 | 57 | 4-(4-chlorophenoxy)phenol | 2,4-dibromopentanoic anilide | 4-[4-(4-chlorophenoxy)phenoxy]-2-pentenoic anilide | m.p. 117° C. | 76.1 | 68.1 |
| 21 | 58 | 4-(3-trifluoromethylphenoxy)phenol | ethyl 3,4-dibromopentanoate | ethyl 4-[4-(3-trifluoromethylphenoxy)phenoxy]-2-pentenoate | $n_D^{20}$ 1.5155 | 95.5 | 84.5 |
| 22 | 59 | 4-(4-nitrophenoxy)phenol | ethyl 2,4-diiodopentanoate | ethyl 4-[4-(4-nitrophenoxy)phenoxy]-2-pentenoate | $n_D^{20}$ 1.5788 | 78.2 | 69.8 |
| 23 | 60 | 4-(4-iodophenoxy)phenol | isopropyl 2,4-dibromopentanoate | isopropyl 4-[4-(4-iodophenoxy)phenoxy]-2-pentenoate | $n_D^{20}$ 1.5753 | 94.6 | 83.9 |
| 24 | 61 | 4-(2-cyanophenoxy)phenol | ethyl 3-bromo-4-chloropentanoate | ethyl 4-[4-(2-cyanophenoxy)phenoxy]-2-pentenoate | $n_D^{20}$ 1.5625 | 85.5 | 75.5 |
| 25 | 62 | 4-(4-methylphenoxy)phenol | ethyl 3,4-dibromohexanoate | ethyl 4-[4-(4-methylphenoxy)phenoxy]-2-hexenoate | $n_D^{20}$ 1.5492 | 94.4 | 86.2 |
| 26 | 63 | 4-(2-chloro-4-trifluoromethylphenoxy)phenol | ethyl 3,4-dibromopentanoate | ethyl 4-[4-(2-chloro-4-trifluoromethylphenoxy)phenoxy]-2-pentenoate | $n_D^{20}$ 1.5283 | 95.1 | 85.1 |
| 27 | 64 | 4-(2-chloro-4-trifluoromethylphenoxy)phenol | β-bromoethyl 3,4-dibromopentanoate | β-bromoethyl 4-[4-(2-chloro-4-trifluoromethylphenoxy)phenoxy]-2-pentenoate | $n_D^{20}$ 1.5436 | 95.1 | 85.8 |
| 28 | 65 | 4-(2-chloro-4-trifluoromethylphenoxy)phenol | allyl 2,4-dichloro-5-methylhexanoate | allyl 4-[4-(2-chloro-4-trifluoromethylphenoxy)phenoxy]-5-methyl-2-hexenoate | $n_D^{20}$ 1.5125 | 77.6 | 70.0 |
| 29 | 66 | 4-(4-trifluoromethyl-2-nitrophenoxy)phenol | ethyl 2,4-dibromopentanoate | ethyl 4-[4-(4-trifluoromethyl-2-nitrophenoxy)phenoxy]-2-pentenoate | $n_D^{20}$ 1.5343 | 92.2 | 82.5 |
| 30 | 67 | 4-(3,5-dichloropyridyl-2-oxy)phenol | methyl 3,4-dibromopentanethioate | methyl 4-[4-(3,5-dichloropyridyl-2-oxy)phenoxy]-2-pentenethioate | $n_D^{20}$ 1.6072 | 93.6 | 82.6 |
| 31 | 68 | 4-(3,5-dichloropyridyl-2-oxy)phenol | sec.-butyl 2,4-diiodohexanoate | sec.-butyl 4-[4-(3,5-dichloropyridyl-2-oxy)phenoxy]-2-hexenoate | $n_D^{20}$ 1.5014 | 71.2 | 65.1 |
| 32 | 69 | 4-(3,5-dichloropyridyl-2-oxy)phenol | allyl 2,4-dibromopentanoate | allyl 4-[4-(3,5-dichloropyridyl-2-oxy)phenoxy]-2-pentenoate | $n_D^{20}$ 1.5706 | 91.6 | 82.8 |
| 33 | 70 | hydroquinone | ethyl 3,4-dibromopentanoate | ethyl 4-(4-hydroxyphenoxy)-2-pentenoate | $n_D^{20}$ 1.5333 | 63.2 | 54.8 |
| 34 | 71 | hydroquinone | n-butyl 2,4-dibromo- | n-butyl 4-(4-hydroxyphe- | $n_D^{20}$ 1.5471 | 61.1 | 54.2 |

TABLE 1-continued

| Example Reaction 1 | Example Reaction 2 | Starting materials Phenol compound | Dihalogen compound | Product Phenoxyalkene derivative | Physical property | Yield (%) Reaction 1 | Yield (%) Reaction 2 |
|---|---|---|---|---|---|---|---|
| 35 | 72 | hydroquinone | allyl 3,4-dichloropentanoate | allyl 4-(4-hydroxyphenoxy)-2-pentenaote | $n_D^{20}$ 1.5683 | 55.2 | 49.4 |
| 36 | 73 | 4-(4-trifluoromethylphenoxy)phenol | 3,4-dibromopentanol | 4-[4-(4-trifluoromethylphenoxy)phenoxy]-2-pentenol | $n_D^{20}$ 1.5330 | 61.0 | 53.9 |
| 37 | 74 | 4-(4-bromophenoxy)phenol | 2,4-dichloropentanol | 4-[4-(4-bromophenoxy)phenoxy]-2-pentenol | $n_D^{20}$ 1.5871 | 44.6 | 38.5 |
| 38 | 75 | 4-(4-trifluoromethylphenoxy)phenol | β-chloroethyl 3,4-dibromopentanoate | β-chloroethyl 4-[4-(4-trifluoromethylphenoxy)phenoxy]-2-pentenoate | m.p. 129–132° C. | 90.3 | 82.9 |
| 39 | 76 | 4-(3,5-dichloropyridyl-2-oxy)phenol | 3,4-dibromopentanoic acid | 4-[4-(3,5-dichloropyridyl-2-oxy)phenoxy]-2-pentenoic acid | m.p. 157–159° C. | 84.1 | 76.7 |
| 40 | 77 | 4-(4-phenoxy)phenol | n-butyl 3,4-dibromopentanoate | n-butyl 4-[4-(4-phenoxy)phenoxy]-2-pentenoate | $n_D^{20}$ 1.5511 | 90.1 | 82.5 |
| 41 | 78 | 4-(5-bromopyridyl-2-oxy)phenol | n-butyl 3,4-dibromopentanoate | n-butyl 4-[4-(5-bromopyridyl-2-oxyl)phenoxy]-2-pentenoate | $n_D^{20}$ 1.5591 | 89.1 | 81.5 |

EXAMPLES 79 to 89

In accordance with the process of Example 1 except replacing tributylethylammonium bromide by various quaternary salts shown in Table 2, ethyl 4-[4-(4-trifluoromethylphenoxy)phenoxy]-2-pentenoate was obtained. The yields in the reactions are shown in Table 2.

TABLE 2

| Example | Quaternary salt | Yield (%) |
|---|---|---|
| 79 | benzyltrimethylammonium chloride | 92.1 |
| 80 | benzyltriethylammonium bromide | 94.0 |
| 81 | benzyltrioctylammonium chloride | 92.9 |
| 82 | benzyltriphenylphosphonium chloride | 93.5 |
| 83 | tetraethylammonium bromide | 93.5 |
| 84 | tetrabutylammonium bromide | 93.3 |
| 85 | tetrahexylammonium bromide | 92.0 |
| 86 | trioctylmethylammonium chloride | 93.0 |
| 87 | tetrabutylphosphonium bromide | 93.9 |
| 88 | methyltriphenylphosphonium bromide | 93.5 |
| 89 | butyltriphenylphosphonium bromide | 93.1 |

EXAMPLES 90 to 97

In accordance with the process of Example 1 except replacing chlorobenzene by various nonpolar solvents shown in Table 3, ethyl 4-[4-(4-trifluoromethylphenoxy)phenoxy]-2-pentenoate was obtained.

The yields in the reactions are shown in Table 3.

TABLE 3

| Example | Solvent | Yield (%) |
|---|---|---|
| 90 | benzene | 93.9 |
| 91 | toluene | 94.0 |
| 92 | xylene | 93.5 |
| 93 | dichlorobenzene | 93.1 |
| 94 | chloroform | 92.7 |
| 95 | carbon tetrachloride | 92.5 |
| 96 | n-hexane | 92.6 |
| 97 | cyclohexane | 92.5 |

EXAMPLES 98–104

In accordance with the process of Example 3 except replacing ethanol by various polar solvents shown in Table 4, ethyl 4-[4-(4-trifluoromethylphenoxy)phenoxy]-2-pentenoate was obtained.

The yields in the reactions are shown in Table 4.

TABLE 4

| Example | Polar solvent | Yield (%) |
|---|---|---|
| 98 | methanol | 80.1 |
| 99 | acetone | 82.1 |
| 100 | methylethyl ketone | 81.5 |
| 101 | diethyl ether | 79.7 |
| 102 | ethyleneglycol dimethyl ether | 82.0 |
| 103 | dimethylformamide | 84.7 |
| 104 | dimethylsulfoxide | 85.0 |

We claim:

1. A process for produding a phenoxyalkene derivative having the formula

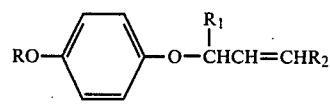

(III)

$$RO-\text{C}_6\text{H}_4-O-\underset{R_1}{\text{CHCH}}=CHR_2$$

wherein R represents a hydrogen atom,

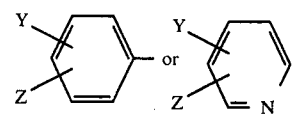

and Y and Z are the same or different and respectively represent a hydrogen atom, trifluoromethyl group, a halogen atom, a lower alkyl group, nitro group or cyano group; $R_1$ represents a hydrogen atom or a lower alkyl group and $R_2$ represents carboxyl, hydroxymethyl, allyloxycarbonyl, a lower alkoxycarbonyl, a lower haloalkoxycarbonyl, a S-lower alkylthiocarboxyl, carbamoyl, a N-lower alkylcarbamoyl or a N-phenylcarbamoyl group which comprises reacting a phenol compound having the formula

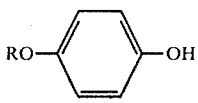

with a dihalogen compound at a molar ratio of 1.0 to 1.5 based on the phenol, having the formula

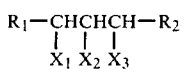

wherein R, $R_1$ and $R_2$ are defined above and $X_1$ represents a halogen atom and $X_2$ and $X_3$ are different and respectively represent a hydrogen atom or a halogen atom, by a simultaneous reaction of an etherification and an unsaturated double bond formation, in the presence of a dehydrogenhalide agent at a molar ratio of 1 to 3 based on the phenol, and a polar solvent or a combination of a non-polar solvent and a quaternary ammonium salt or a quaternary phosphonium salt, at a molar ratio of 0.005 to 0.05 based on the phenol, at a temperature between 30° to 150° C.

2. A process according to claim 1 wherein the reaction is carried out in a presence of a quaternary ammonium salt or a quaternary phosphonium salt at a molar ratio of 0.005 to 0.05 based on the phenol compound (I).

3. A process according to claim 1 wherein the reaction is carried out in a polar solvent and then polar solvent is distilled off and the product is purified.

4. A process according to claim 1 wherein the dihalogen compound (II) is the compound having the formula (II) wherein $R_1$ represents a hydrogen atom; a lower alkyl group selected from methyl, ethyl, propyl, isopropyl, butyl and isobutyl group; $R_2$ represents carboxyl, hydroxymethyl, allyloxycarbonyl; a lower alkoxycarbonyl selected from methoxycarbonyl, ethoxycarbonyl, isopropoxycarbonyl, and sec.-butoxycarbonyl group; a lower haloalkoxycarbonyl group selected from $\beta$-chloroethoxycarbonyl, $\beta$-bromoethoxycarbonyl, $\alpha,\beta$-dibromopropyloxycarbonyl, $\alpha,\beta$-dibromopropyloxycarbonyl and $\beta,\beta'$-dibromoisopropyloxycarbonyl group; a S-lower alkylthiocarboxyl group selected from S-methylthiocarboxyl, S-ethylthiocarboxyl and S-butylthiocarboxyl group; carbamoyl group; a N-lower alkylcarbamoyl group selected from N-methylcarbamoyl, N-ethylcarbamoyl, N-isopropylcarbamoyl and N-isobutylcarbamoyl group; or a N-phenylcarbamoyl group and $X_1$, $X_2$ and $X_3$ are halogen atom selected from chlorine atom, bromine atom, and iodine atom.

* * * * *